United States Patent [19]
Démarcq et al.

[11] 4,145,305
[45] Mar. 20, 1979

[54] PHOSPHORUS ACTIVATORS FOR PERCOMPOUNDS

[75] Inventors: Michel Démarcq, Lyons; Michel Bakes, La Celle Saint Cloud; Marie-Christine Daude-Lagrave, Paris, all of France

[73] Assignee: Produits Chimiques Ugine Kuhlmann, Paris, France

[21] Appl. No.: 802,515

[22] Filed: Jun. 1, 1977

[30] Foreign Application Priority Data

Jun. 4, 1976 [FR] France .................. 76 16927

[51] Int. Cl.² ............ C11D 3/395; C11D 7/54; D06L 3/02
[52] U.S. Cl. .................. 252/186; 252/95; 252/99; 423/272; 560/264; 8/111
[58] Field of Search ............ 252/186, 95, 97, 99; 8/107; 560/264; 423/272, 233

[56] References Cited

U.S. PATENT DOCUMENTS

| | | | |
|---|---|---|---|
| 3,073,666 | 1/1963 | Dithmar et al. | 8/111 |
| 3,459,669 | 8/1969 | Das et al. | 252/99 |
| 3,649,164 | 3/1972 | Yelin et al. | 252/186 |
| 3,655,573 | 4/1972 | Carlson | 252/186 |
| 3,982,892 | 9/1976 | Gray | 252/186 |

*Primary Examiner*—Benjamin R. Padgett
*Assistant Examiner*—Irwin Gluck
*Attorney, Agent, or Firm*—Brooks, Haidt, Haffner & Delahunty

[57] ABSTRACT

Phosphorus-containing activators for percompounds, the activators being tris(acetoxymethyl) phosphine oxide and its precursors including tris(acetoxymethyl) phosphine and tetrakis(acetoxymethyl) phosphonium compounds, together with the use of such activators with percompounds for oxidizing or bleaching such as in bleaching fibers, oils, fats, and waxes, cosmetological treatment of hair and skin, metallic surface passivation, and purification, disinfection and sterilization techniques, the use of such activators providing more rapid action at a given temperature or equal activity at a lower temperature.

4 Claims, No Drawings

PHOSPHORUS ACTIVATORS FOR PERCOMPOUNDS

BACKGROUND OF THE INVENTION

The present invention relates to the use of certain phosphorus compound activators for percompounds, and more particularly, it relates to the use of tris-(acetoxymethyl)-phosphine oxide and certain of its precursors as activators for hydrogen peroxide and its addition compounds with organic substances as well as to mineral persalts.

Aqueous solutions of percompounds are used as oxidizing agents and bleaching agents, but they do not generally become active except at temperatures above 70° C., and more preferably at temperatures of from 80° to 100° C. The prior art describes a number of products showing the property of acting as percompound activators, that is, permitting an oxidizing action or bleaching action which is more rapid than that usually observed or which is also developed under conditions of temperature which are much milder than those necessary for use in their absence. All of these compounds are characterized by the fact that they have one or more perhydrolysable functions.

In the field of bleaching, a certain number of activator compounds have undergone the beginning of commercial use. The literature on this subject makes mention principally of poly-N-acetyl heterocyclic compounds of the hydantoin, glycoluril, benzimidazole and diketopiperazine types. Nevertheless, their development has not been pursued because these substances present the major difficulty of being unstable in ambient humidity and spontaneously hydrolyzing. Thus, their activator properties are rapidly destroyed.

Moreover, these products necessitate special precautions in storage and upon addition to certain ingredients such as those included, for example, in the usual detergent powder compositions. Various solutions have been proposed to alleviate these deficiencies, such as coating, separate packaging, or addition of dehydrating agents, but none of these have given satisfaction, either because these solutions pose technical problems for practical use or because they occasion a considerable increase in the price of manufacturing the active material.

There accordingly exists a commercial requirement to provide percompound activators which will be more stable over a period of time in the solid state under normal conditions of storage and packaging.

THE INVENTION

The present invention overcomes the prior art deficiencies and permits the commercial utilization of percompounds through the use of phosphorus-containing percompound activators selected from the group consisting of tris(acetoxymethyl)phosphine oxide having the formula:

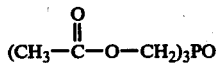

and two of its precursors, tris(acetoxymethyl)phosphine having the formula:

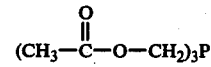

and tetrakis(acetoxymethyl)phosphonium compounds having the formula:

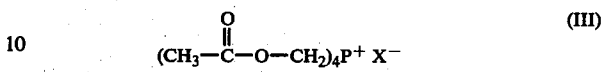

where $X^-$ is an inorganic or organic anion, described hereinafter. Thus, the present invention contemplates the activators and their use in improving the activity of percompounds, as described herein.

The phosphine is justifiably considered as a precursor because in the presence of a solution or a suspension of percompounds, it is rapidly oxidized to the corresponding phosphine oxide (I). Phosphonium salts (III) can also be considered as precursors of (I) because they are transformed rapidly to the phosphine (II) which is itself a precursor of (I) when the contact takes place in a weakly or strongly basic environment. (See Mironova, Z. N.; Tsvetkov, E. W.; et al, *Zh. obshchei Khim.* 1967, 37, 2747-52 and U.S. Pat. Nos. 3,725,001 and 3,845,107). The anion in phosphonium salts (III) can be, as taught above, inorganic including halides, preferably the chloride and bromide, hydroxide, sulfate, phosphate and the like, or organic, particularly salts of lower carboxylic acids such as formate, acetate, oxalate and the like. A preferred halide is the chloride.

The invention also encompasses the use as percompound activators of mixtures in all proportions of two or more of phosphorus derivatives (I), (II), and (III).

According to the particular need, one can operate over a wide range of activator/percompound. A molar ratio of activator to percompound between 0.1 and 10 is desirable in certain embodiments of the invention. A particularly advantageous method for the use of such activators according to the present invention consists of their addition to a percompound in the ratio of about 0.33 moles per mole of percompound to be activated.

The activators according to the present invention can be used in all cases where a percompound is employed to obtain an oxidizing or bleaching action. The percompounds activated according to the present invention include hydrogen peroxide and its addition products with organic and inorganic compounds. Thus, the activators can be used with organic percompounds such as the addition products of hydrogen peroxide with urea, dicyclohexylamine, and the like and with inorganic compounds, such as perborates, percarbonates, perphosphates, and the like.

For instance, the compounds of this invention can be used with percompounds in bleaches for textile fibers, oils, fats, and waxes, for cosmetic treatment of hair and skin, for passivation of metallic surfaces, and in purification, disinfection and sterilization techniques. The activators of the present invention are added to a percompound or to a composition containing one or more percompounds. For example, the present activators can be added to detergent powders to permit, without changing the temperature, a more rapid bleaching or oxidizing effect. The compounds of this invention equally permit operation at lower temperatures to obtain the same final bleaching effect.

For example, in the presence of sodium perborate in a washing environment, the activators of this invention permit one to obtain, at temperatures of 30° to 50° C., a bleaching action substantially equivalent to that obtained in their absence at elevated temperatures of about 80° C.

The following examples are given to illustrate embodiments of the invention as it is presently preferred to practice it. It will be understood that these examples are illustrative, and the invention is not to be considered as restricted thereto except as indicated in the appended Claims.

EXAMPLE I

Into a compartment of an "AHIBA" water bath maintained at 40° C., 250 ml of an aqueous solution containing 5 grams per liter of a washing powder having the following composition is introduced:

| Ingredient | Percent (by weight) |
| --- | --- |
| $Na_2SiO_3$ | 5.34 |
| $Na_2SO_4$ | 7.25 |
| $Na_2CO_3$ | 2.65 |
| $Na_2HPO_4$ | 0.96 |
| $Na_4P_2O_7$ | 3.99 |
| $Na_5P_3O_{10}$ | 30.41 |
| $NaPO_3$ | 11.92 |
| $H_2O$ | 18.9 |
| Surfactants | 14 |
| Miscellaneous to make | 100 | and 1.7 g/L of sodium perborate tetrahydrate. Another compartment of the bath is charged with the same solution additionally containing 1 g/L of tris-(acetoxymethyl)phosphine. Into each compartment is then placed a swatch of "EMPA" cotton impregnated with wine stains standardized by the Saint-Gall, Switzerland, laboratory.

After 15 minutes of washing at 40° C., the swatches are rinsed in a stream of cold water and then dried at room temperature.

The bleaching power is defined by the difference between the whiteness indices (measured through the use of a Carl Zeiss "ELREPHO" spectrophotometer, having a No. 6 filter) before and after washing. The values are recorded in percentage, with a maximum whiteness of 100%, according to the following formula:

$$\text{percent whitening} = \frac{\text{Whiteness Change}}{100 - \text{Initial Whiteness}} \times 100$$

Using the foregoing formula, it is found that the whitening without the activator is 43.2%, while the whitening with the activator is 63%.

EXAMPLE II

Under the same conditions as in Example I, tris-(acetoxymethyl)phosphine oxide is used at a concentration of one gram per liter. Under these conditions, the whitening without activator is 43.2%; the whitening with activator is 64%.

EXAMPLE III

The test of Example I is repeated using tetrakis-(acetoxymethyl)phosphonium chloride at a concentration of one gram per liter. Under these conditions, the whitening without activator is 35.7%; the whitening with activator is 51.8%.

What is claimed is:

1. Processes for activating percompounds, which processes comprise associating with at least one percompound a quantity of at least one phosphorus-containing activator sufficient to activate the percompound component, the activator being tris(acetoxymethyl)-phosphine oxide having the formula $$(CH_3C(=O)-O-CH_2)_3PO;$$ 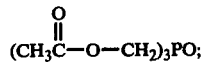

tris(acetoxymethyl)phosphine having the formula $$(CH_3C(=O)-O-CH_2)_3P$$ 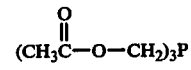

or a tetrakis(acetoxymethyl)phosphonium compound having the formula $$(CH_3C(=O)-O-CH_2)_4P^+X^-$$

wherein X is an organic or inorganic ion.

2. A process according to claim 1 wherein the percompound is hydrogen proxide or one of its addition compounds.

3. A process according to claim 2 wherein the molar ratio of activator to percompound is from 0.1 to 10.

4. A process according to claim 2 wherein the molar ratio of activator to percompound is about 0.33.

* * * * *